United States Patent
Weisbart et al.

(10) Patent No.: US 8,236,037 B2
(45) Date of Patent: Aug. 7, 2012

(54) SCALAR LASER THERAPY APPARATUS

(76) Inventors: Paul Weisbart, Haiku, HI (US); Lillie Weisbart, Haiku, HI (US)

( * ) Notice: Subject to any disclaimer, the term of this patent is extended or adjusted under 35 U.S.C. 154(b) by 769 days.

(21) Appl. No.: 12/258,082

(22) Filed: Oct. 24, 2008

(65) Prior Publication Data

US 2009/0112296 A1    Apr. 30, 2009

Related U.S. Application Data

(60) Provisional application No. 60/982,294, filed on Oct. 24, 2007.

(51) Int. Cl.
*A61N 5/067*    (2006.01)

(52) U.S. Cl. .............................. 607/89; 607/88; 606/9

(58) Field of Classification Search ... 606/9; 607/88–91
See application file for complete search history.

(56) References Cited

U.S. PATENT DOCUMENTS

| | | | |
|---|---|---|---|
| 4,649,935 A | 3/1987 | Charmillot et al. | |
| 4,765,322 A | 8/1988 | Charmillot et al. | |
| 4,930,504 A | 6/1990 | Diamantopoulos et al. | |
| 4,951,663 A | 8/1990 | L'Esperance, Jr. | |
| 5,358,503 A | 10/1994 | Bertwell et al. | |
| 5,464,436 A | 11/1995 | Smith | |
| 5,549,660 A | 8/1996 | Mendes et al. | |
| 5,616,140 A | 4/1997 | Prescott | |
| 5,755,752 A | 5/1998 | Segal | |
| 5,800,479 A | 9/1998 | Thiberg | |
| 5,830,211 A | 11/1998 | Santana et al. | |
| 6,019,482 A | 2/2000 | Everett | |
| 6,187,029 B1 | 2/2001 | Shapiro et al. | |
| 6,443,978 B1 | 9/2002 | Zharov | |
| 6,454,791 B1 * | 9/2002 | Prescott | 607/89 |
| 6,602,275 B1 | 8/2003 | Sullivan | |
| 6,702,837 B2 | 3/2004 | Gutwein | |
| 6,872,221 B2 | 3/2005 | Lytle | |
| 2002/0198575 A1 * | 12/2002 | Sullivan | 607/88 |
| 2004/0030370 A1 | 2/2004 | Lytle | |
| 2008/0183161 A1 | 7/2008 | Walneck et al. | |
| 2009/0227996 A1 * | 9/2009 | Powell et al. | 606/9 |

* cited by examiner

*Primary Examiner* — Henry M Johnson, III
*Assistant Examiner* — Jeffrey Lipitz
(74) *Attorney, Agent, or Firm* — Banner & Witcoff, Ltd.

(57) ABSTRACT

There is disclosed a new low-level laser therapy apparatus and method of treating tissue. The invention includes a laser system that uses laser diodes and/or alternatively light emitting diodes (LED's), or both, and a digital interface that gives the operator the ability to generate sine waves or scalar waves as opposed to the simple on/off square waves. The invention also enables the operator to modulate not only the frequency, but also other wave characteristics such as the amplitude and phase. In one aspect, the invention involves modulating the phase relationship between multiple waves by taking one channel or wave which is pulsed through the laser system and then running a second channel or wave in relationship to the first channel, thereby creating a phased relationship, which has been discovered to provide a therapeutic and quantum healing effect on tissue. In one exemplary embodiment, the laser system of the invention may have a phase relationship of approximately 180 degrees which provides a beneficial therapeutic and quantum healing effect and, in particular, neutralizes or deletes cellular memory.

15 Claims, 3 Drawing Sheets

SCALAR LASER THERAPY APPARATUS

CROSS-REFERENCE TO RELATED APPLICATION

This Non-Provisional Application claims benefit to U.S. Provisional Application Ser. No. 60/982,294, filed Oct. 24, 2007.

FIELD OF THE INVENTION

The present invention relates generally to lasers for the treatment of human tissue and, more particularly, to low level lasers and light emitting diodes (LED's) that are used to provide a therapeutic and quantum effect to treat human tissue for health, rejuvenation and wellness, and the deletion of cellular memory.

BACKGROUND OF THE INVENTION

It is known that lasers and LED'S may be used to deliver energy to targeted tissue to aid in the repair of tissue damage. The lasers and LED's may also be used to provide beneficial therapeutic effect in the treatment of neurological and soft tissue conditions. More specifically, the lasers and LED's deliver energy to targeted tissue, penetrating the layers of skin to reach internal tissues to produce a specific, non-thermal photochemical effect at the cellular level. This type of therapy is non-invasive and avoids the potential side effects of drug therapy.

There remains, however, a need in the art for better laser therapy treatment. The present invention provides such improved treatment and is directed to a new low-level laser therapy apparatus and method of treating tissue.

SUMMARY OF THE INVENTION

The following presents a general summary of aspects of the invention in order to provide a basic understanding of the invention and various features of it. This summary is not intended to limit the scope of the invention in any way, but simply provides a general overview and context for the more detailed description that follows.

The present invention is directed to a hand-held laser system that uses laser diodes and/or alternatively LED's, or both, to provide energy to targeted tissue to provide a beneficial therapeutic and quantum healing effect, and to neutralize or delete cellular memory. The hand-held laser system includes a digital interface that gives the operator the ability to generate sine waves or scalar waves at a particular frequency, as opposed to the simple on/off square waves that non-digital systems use. The laser system also enables the operator to modulate not only the frequency, but also other wave characteristics such as the amplitude and phase. One aspect of the invention involves modulating the phase relationship between multiple waves in the laser system. In other words, the invention takes one channel or wave (frequency) which is pulsed through the laser and then runs a second channel or wave in relationship to the first channel. This is referred to as the phase relationship of the waves and is measured between 0 and 360. It has been discovered that the laser system of the invention having a phase relationship between waves, such as sine and scalar waves, has a therapeutic and quantum healing effect on tissue. In one exemplary embodiment, it has been discovered that the laser system of the invention having a phase relationship of approximately 180 degrees provides a desired therapeutic and quantum healing effect and, in particular, neutralizes or deletes cellular memory.

Other features and advantages of the invention will become apparent to those skilled in the art upon review of the following detailed description, claims and drawings in which like numerals are used to designate like features.

Figure 1:
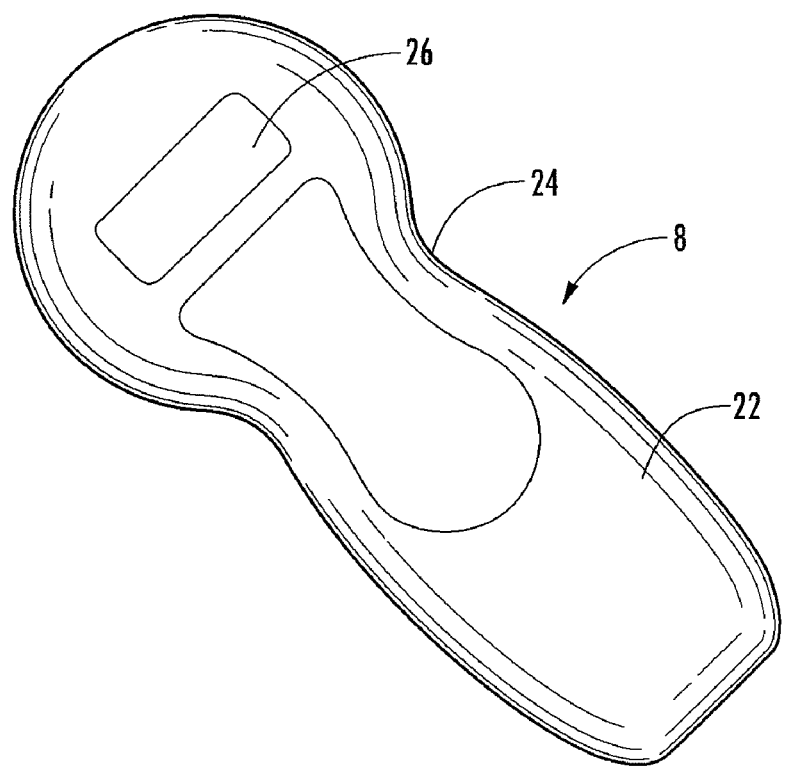
FIG. 1 is a top plan view of an exemplary embodiment of a laser therapy apparatus of the present invention.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE EMBODIMENTS

Figure 2:
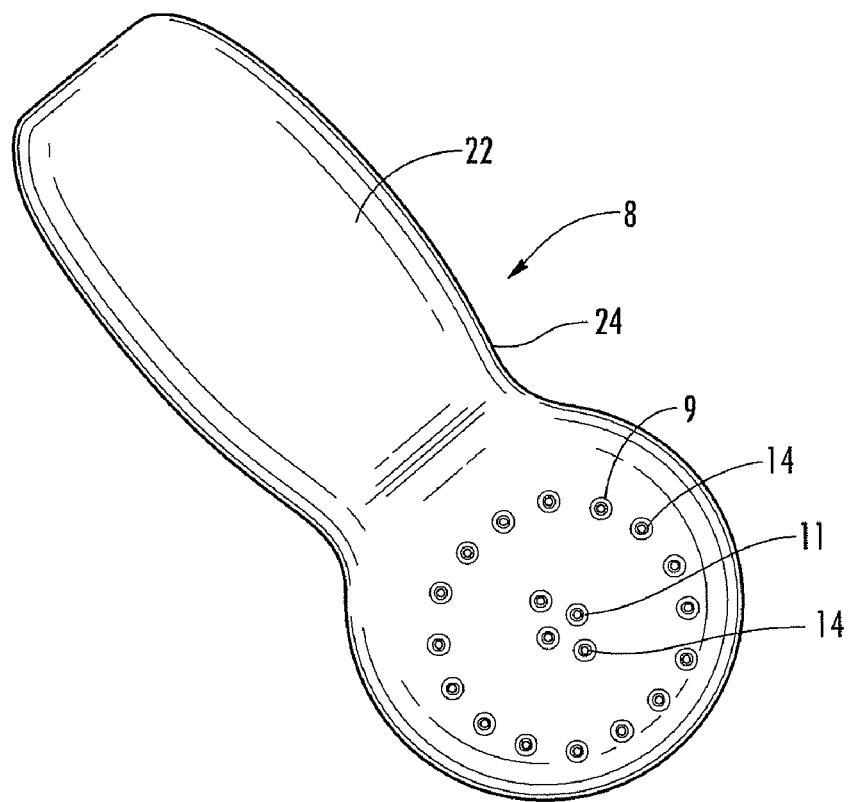
FIG. 2 is a bottom view of the laser apparatus of FIG. 1, illustrating an exemplary laser diode and LED pattern.

Referring to FIGS. 1 and 2, there is shown an exemplary hand-held, battery-powered laser therapy apparatus 8 of the invention which includes a plurality of laser diodes and/or LED's emitting light at particular wavelengths for the purpose of providing energy to the human body in therapeutic applications. The exemplary therapy apparatus 8 may include on one side a plurality of laser diodes and/or LED's 14 arranged in a particular pattern that emit visible and near-infrared radiation to prove therapeutic and quantum healing effect and to neutralize or delete cellular memory. This is accomplished by modulating the phase relationship between multiple waves in the laser system. It has been determined that the laser system of the invention having a phase relationship between waves, such as sine and scalar waves, has a desired therapeutic and quantum healing effect on tissue. As further explained below, a laser system having a phase relationship of approximately 180 degrees provides this desired therapeutic and healing effect, and neutralizes or deletes cellular memory.

Figure 3:
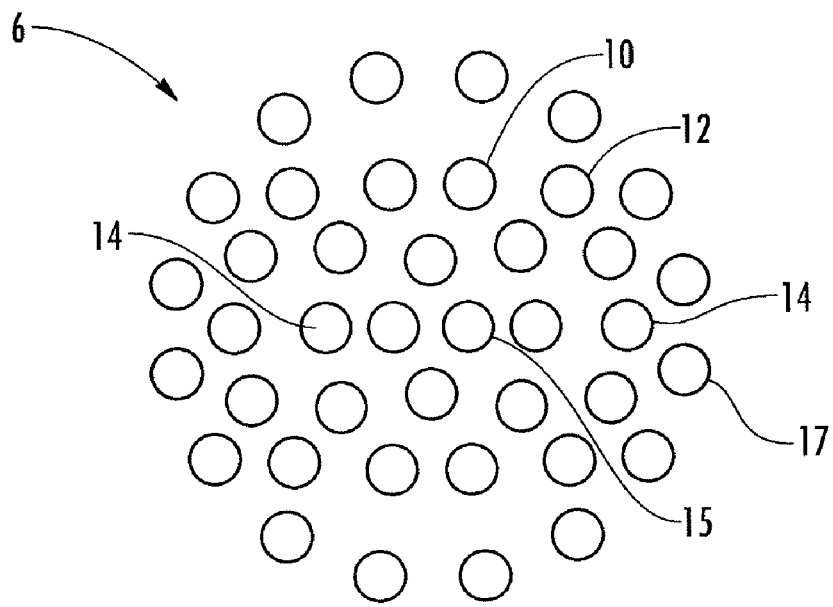
FIG. 3 is a schematic of an alternative laser diode and LED pattern.

In one embodiment, and as shown in FIG. 3, the laser therapy apparatus 8 may include at least two tracks 10, 12 of spaced-apart laser diodes and/or LED'S 14 with each track having approximately ten laser diodes. The two tracks 10, 12 may be configured in a concentric pattern, or other suitable patterns. The number of diodes 14 may vary depending on the desired application. In one embodiment of the invention, the phase relationship between the tracks 10, 12 may be set to approximately 180 degrees, or set to any other suitable phase relationship. By using this configuration of diodes with the same frequencies being pulsed through each track, but with different phase relationships between the tracks, studies have shown that the laser therapy apparatus 8 will provide a very unique and beneficial healing and rejuvenation effect, and the deletion of cellular memory.

In an exemplary embodiment, the diodes 14 may include one or more red (650 nm) laser diodes each having a power of 5 mW. The diodes 14 may also include one or more infrared (780 nm) laser diodes each having a power of 5 mW. Additionally, the diodes 14 may include one or more violet (420 nm) LED's each having a power of 1000 mcd. The apparatus 8 may have a frequency range from 1 Hz to 20,000 Hz sine wave, and 40 Hz square wave. The diodes 14 may be mounted to or in the apparatus 8 and may be configured such that laser or LED beams emitted therefrom travel parallel to each other, or intersect at a short distance away from the apparatus 8.

In an alternative embodiment, the apparatus 8 may include one laser diode surrounded by four LED's. With this embodiment, the laser diode may be one higher power than the four LED's. In this embodiment, the laser diode may define one circuit, while the surrounding four LED's define a separate circuit. In an alternative aspect, there may be up to five or more LED/laser clusters arranged on the apparatus 8. Each cluster will have its own control capability independent of the others. It should be understood by those skilled in the art that numerous combinations or laser diodes and LED's are possible with the teachings of the invention, as further illustrated below.

In one embodiment, the apparatus 8 may define a body portion 22 that may be fabricated, for example, from a molded plastic material, such as ABS/poly blend. The body portion 22 may define a contoured grip portion 24 that permits the operator to more easily handle the laser apparatus. The body portion 22 will contain the circuitry that controls the operation of the laser apparatus 8 and the diodes 14. The body portion also contains a battery, not shown, such as a lithium ion rechargeable battery. The body portion 22 may further contain charging circuitry to allow a simple external power source to be used for charging.

In an exemplary embodiment, and as shown in FIG. 1, the laser apparatus 8 may include on top of the unit a display 26, such as an LCD character display and keypad readout, to allow the user to select from many therapy modes. Additionally, light intensity, flash frequency, and flash duration may be adjusted for each mode. The display may also provide such information as projected time of operation remaining based on battery capacity, and may provide a visual alarm indicating the number of minutes remaining when capacity runs low. The display also enables the operator to modulate not only the frequency, but also other wave characteristics such as the amplitude and phase.

Referring to FIG. 2, there is shown an alternative arrangement of the plurality of spaced apart laser diodes and/or LED's 14 positioned in a concentric pattern on the body portion 22. As depicted, a first outer ring 9 of diodes 14 may be positioned near the periphery of the body portion and define one track, and a second diamond-shaped pattern 11 of diodes 14 may be positioned near the center of the body portion and define a second track. As indicated above, any number of combinations of laser diodes and/or LED's 14 may be used as part of the outer ring 9 or the diamond-shaped pattern 11. In the embodiment depicted in FIG. 2, the first outer ring 9 may include LED's, and the second diamond-shaped pattern 11 may include laser diodes.

Referring to FIG. 3, in another aspect of the invention, and as explained above, the laser apparatus 8 may have a pattern 6 that includes at least two tracks 10, 12 of spaced apart laser diodes and/or LED'S 14. The pattern may also include an inner diamond-shape arrangement 15 of diodes 14 and an outer ring 17 of diodes 14, each defining their own respective track. The two tracks 10, 12 may be configured in a concentric pattern, or other suitable patterns. The phase relationship between these two tracks may be set to approximately 180 degrees to provide the desired therapeutic effect. By using this configuration of diodes with the same frequencies being pulsed through each track, but with different phase relationships between the tracks, the laser system will provide a beneficial healing effect, and will result in the deletion of cellular memory. Each track will have its own circuitry for control capability independent of the other track of diodes. In the embodiment of FIG. 3, the tracks 10, 12 will include laser diodes and the inner diamond-shaped arrangement 15 and outer ring 17 will include LED's, all being arranged concentrically with each other and all on their own respective tracks. It should be understood that this diode configuration and the particular diodes used therein is merely exemplary of the numerous possible laser diode and/or LED patterns.

Figure 4:
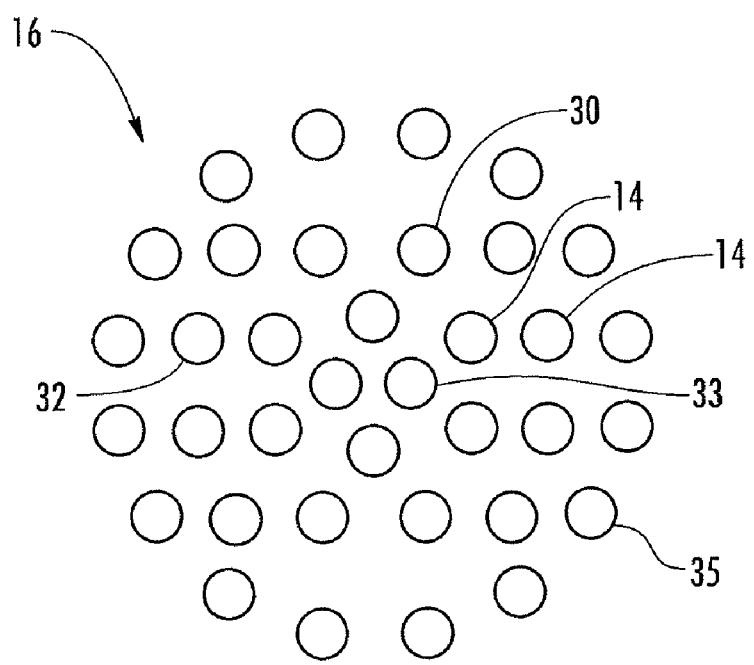
FIG. 4 is a schematic of another alternative laser diode and LED pattern.

Referring to FIG. 4, in yet another aspect of the invention, the laser apparatus 8 may have a pattern 16 that includes two tracks 30, 32 of spaced apart laser diodes and/or LED'S 14. In this embodiment, each track may have approximately eight laser diodes. The pattern 16 may also have an inner diamond-shaped arrangement 33 of diodes defining a track and an outer ring 35 of diodes also defining a track. The two tracks 30, 32 may be configured in a concentric pattern, or other suitable patterns. Similar to the embodiment of FIG. 3, the phase relationship between these two tracks may be set to approximately 180 degrees, or set to any other suitable phase relationship. Again, by using this configuration of diodes with the same frequencies being pulsed through each track, but with different phase relationships between the tracks, the laser system will provide a beneficial healing effect, and the deletion of cellular memory. Also again, each track of diodes will have its own circuitry for control capability independent of the other track of diodes. In the embodiment of FIG. 4, the tracks 30, 32 will include laser diodes, and the inner diamond-shaped arrangement 33 and outer ring 35 will include LED's. Again, the particular laser diode and/or LED's used with the depicted pattern 16 may vary.

Figure 5:
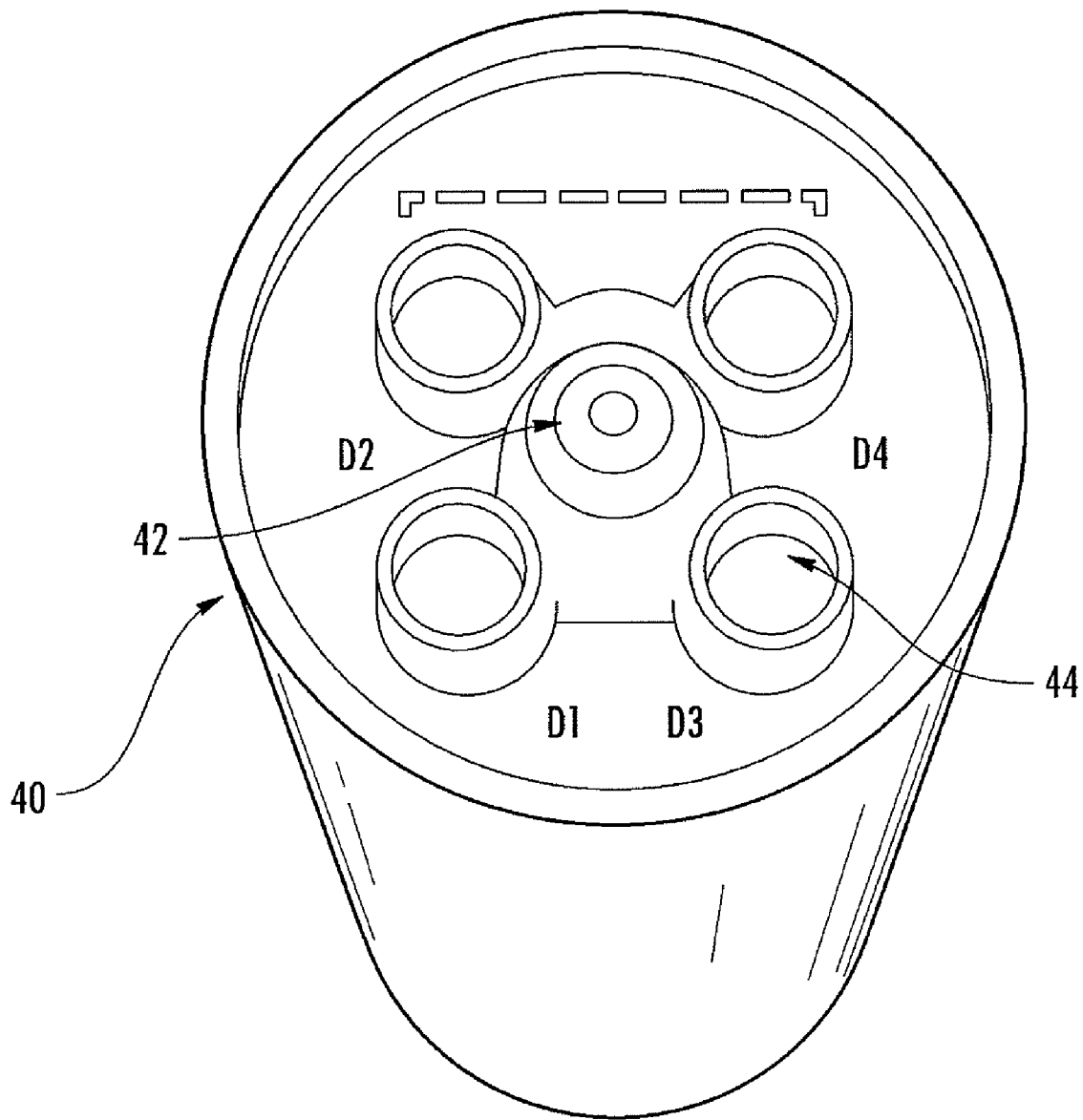
FIG. 5 is a top view of an exemplary laser therapy probe of the present invention.

In an alternative aspect, a higher power laser probe 40 (FIG. 5) may be coupled to the laser therapy apparatus 8 to provide precision therapy applications. This laser probe may be an accessory attachment to the apparatus 8 and may be powered from the apparatus 8. Referring to FIG. 5, the laser probe 40 may define an elongated body that may be handheld. The probe 40 may include any number of laser diodes 42 and/or LED's 44. In an exemplary embodiment, the probe 40 may define a diode pattern that includes a laser diode 42 defining a first track surrounded by four LED's 44 which define a second track. It should be understood by those skilled in the art that other diode patterns are possible. In one embodiment, the probe diodes may include one or more red (650 nm) laser diodes each having a power of 100 mW. The diodes may also include one or more infrared (780 nm) laser diodes each having a power of 100 mW. Also, the diodes may include one or more 405 nm laser diodes each having a power of 60 mW. Additionally, the diodes may include one or more violet (420 nm) LED's. Again, the particular laser diodes and/or LED's used with the probe may vary. Similar to the laser apparatus 8, the phase relationship between the diodes used with the probe 40 may be set to approximately 180 degrees, or set to any other suitable phase relationship. Again, by using this configuration of diodes with the same frequencies being pulsed through each track, but with different phase relationships between the tracks, such as 180 degrees phase difference, the laser probe 40 will provide a beneficial healing effect, and the deletion of cellular memory. Also similar to the laser apparatus 8, each track of diodes will have its own circuitry for control capability independent of the other track of diodes.

Variations and modifications of the foregoing are within the scope of the present invention. It should be understood that the invention disclosed and defined herein extends to all alternative combinations of two or more of the individual features mentioned or evident from the text and/or drawings. All of these different combinations constitute various alternative aspects of the present invention. The claims are to be construed to include alternative embodiments to the extent permitted by the prior art. Various features of the invention are set forth in the following claims.

What is claimed is:

1. A laser therapy apparatus comprising:
   a plurality of laser diodes configured on a housing body, wherein the laser diodes include red, infrared and/or violet diodes,
   control circuitry to control, the operation of the laser diodes,
   the plurality of laser diodes defining a first track and a second track,
   the first track and second track are arranged concentrically of each other, the control circuitry digitally controlling the first track and second track independently of each other,
   the control circuitry controlling the first track of laser diodes to provide a first sine waveform having a first wave phase,
   the control circuitry controlling the second track of laser diodes to provide a second sine waveform having a second wave phase, and
   the control circuitry digitally phase modulating the first wave phase 180 degrees in relation to the second wave phase to provide therapeutic and quantum healing effect and/or to neutralize or delete cellular memory.

2. The laser therapy apparatus of claim 1, wherein some of the laser diodes have a wavelength of 650 nm.

3. The laser therapy apparatus of claim 2, wherein the laser diodes have a power output of 5 mW.

4. The laser therapy apparatus of claim 1, wherein some of the laser diodes have a wavelength of 780 nm.

5. The laser therapy apparatus of claim 4, wherein the laser diodes have a power output of 100 mW.

6. The laser therapy apparatus of claim 1, further comprising laser diodes having a wavelength range of between 405 nm and 420 nm.

7. The laser therapy apparatus of claim 1, wherein frequencies between 1 and 20,000 Hz are pulsed through the laser therapy apparatus.

8. The laser therapy apparatus of claim 1, further comprising a plurality of laser diodes defining a diamond shape and concentrically positioned within the first track.

9. The laser therapy apparatus of claim 1, wherein the plurality of laser diodes defining a diamond shaped pattern have a wavelength of between 405 nm and 420 nm.

10. The laser therapy apparatus of claim 1, further comprising a plurality of laser diodes configured in a ring around the first track and the second track.

11. The laser therapy apparatus of claim 1, further comprising a laser probe attached to the laser therapy apparatus and powered by the laser therapy apparatus, the laser probe including a plurality of laser diodes configured on the probe.

12. The laser therapy apparatus of claim 11, wherein the plurality of probe laser diodes include a first probe laser diode powered by a first sine waveform having a probe first phase and surrounded by multiple probe laser diodes powered by a second sine waveform having a probe second phase, and the control circuitry digitally phase modulating the probe first phase 180 degrees in relation to the probe second phase to provide therapeutic effect.

13. The laser therapy apparatus of claim 1, further comprising an LCD display configured on the housing body.

14. A laser therapy apparatus comprising:
    a plurality of laser diodes configured on a housing body,
    control circuitry to control the operation of the laser diodes,
    the plurality of laser diodes including a first track of laser diodes and a second track of laser diodes,
    the control circuitry controlling the first track of laser diodes to provide a first sine waveform having a first phase,
    the control circuitry controlling the second track of laser diodes to provide a second sine waveform having a second phase, and
    the control circuitry digitally phase modulating the first wave phase 180 degrees in relation to the second wave phase to provide therapeutic and quantum healing effect and/or to neutralize or delete cellular memory, and
    the first track and second track are arranged concentrically of each other, and the control circuitry digitally controlling the first track and second track independently of each other.

15. A laser therapy apparatus comprising:
    a plurality of laser diodes configured on a housing body,
    the plurality of laser diodes define a first track of laser diodes and a second track of laser diodes,
    a digital interface to control the operation of the laser diodes,
    the digital interface controlling the first track of laser diodes to provide a first sine waveform having a first wave phase,
    the digital interface controlling the second track of laser diodes to provide a second sine waveform having a second wave phase, and
    the digital interface controlling the phase modulation of the first wave phase 180 degrees in relation to the second wave phase to provide therapeutic and quantum healing effect and/or to neutralize or delete cellular memory.

* * * * *